United States Patent
Pugh et al.

(10) Patent No.: US 8,941,488 B2
(45) Date of Patent: Jan. 27, 2015

(54) SYSTEM AND METHOD FOR A PROCESSOR CONTROLLED OPHTHALMIC LENS

(71) Applicant: Johnson & Johnson Vision Care, Inc., Jacksonville, FL (US)

(72) Inventors: Randall B. Pugh, St. Johns, FL (US); Adam Toner, Jacksonville, FL (US); Frederick A. Flitsch, New Windsor, NY (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 18 days.

(21) Appl. No.: 13/896,653

(22) Filed: May 17, 2013

(65) Prior Publication Data

US 2014/0340630 A1    Nov. 20, 2014

(51) Int. Cl.
  *G08B 1/08* (2006.01)
  *G02C 11/00* (2006.01)
(52) U.S. Cl.
  CPC ................................ *G02C 11/10* (2013.01)
  USPC ............................... 340/539.12; 340/539.14
(58) Field of Classification Search
  USPC ............ 340/539.12, 539.14, 539.22, 539.26, 340/545.2, 545.3, 542.4, 545.5, 5.1
  See application file for complete search history.

(56) References Cited

U.S. PATENT DOCUMENTS

| | | | |
|---|---|---|---|
| 2003/0021601 A1 | 1/2003 | Goldstein | |
| 2006/0146281 A1 | 7/2006 | Goodall et al. | |
| 2006/0267768 A1* | 11/2006 | Sabeta | 340/572.1 |
| 2009/0033863 A1 | 2/2009 | Blum et al. | |
| 2010/0324476 A1* | 12/2010 | Boukhny et al. | 604/65 |

FOREIGN PATENT DOCUMENTS

| | | |
|---|---|---|
| EP | 2620802 A1 | 7/2013 |
| WO | WO 2013059656 A2 | 4/2013 |

OTHER PUBLICATIONS

PCT International Search Report for PCT/US2014/038061 Date of Mailing Aug. 27, 2014 Datea of Completion Aug. 20, 2014.

* cited by examiner

Primary Examiner — Hung Dang

(57) ABSTRACT

A method and system for the calibration and operation of a processor controlled ophthalmic lens is described. More specifically, the system comprising an interactive wireless device used to personalize the control and activation of one or more functions and/or components of the processor controlled ophthalmic lens. In some embodiments, the personalization may include calibrating the functions and/or components using feedback from the user using the interactive wireless device in response to measured conditions by one or more sensors included in the processor controlled ophthalmic lens.

20 Claims, 5 Drawing Sheets

SYSTEM AND METHOD FOR A PROCESSOR CONTROLLED OPHTHALMIC LENS

TECHNICAL FIELD

The disclosure generally relates to the control of an energized ophthalmic lens having more than one sensor, and more particularly, to a system comprising an interactive wireless device used to personalize and/or calibrate operation and activation protocols controlling a function/component of the energized ophthalmic lens.

BACKGROUND

Traditionally, ophthalmic devices, such as a hydrogel lens, an intraocular lens or a punctal plug, include corrective, cosmetic or therapeutic qualities. A contact lens, for example, may provide vision correcting functionality, cosmetic enhancement, and/or therapeutic effects. Each function is provided by a characteristic of the contact lens. For example, a refractive quality may provide a vision corrective function, a pigment may provide a cosmetic enhancement, and an active agent may provide a therapeutic functionality.

More recently, novel ophthalmic devices based on energized ophthalmic inserts have been described. These devices may use the energization function to power active optical components. Moreover, as electronic devices continue to be miniaturized, it is becoming increasingly more likely to create wearable or embeddable microelectronic devices for ophthalmic lenses with various functionalities. For example, an ophthalmic lens may incorporate a lens assembly having an electronically adjustable focus to augment or enhance performance of the eye. In another example, either with or without adjustable focus, a wearable ophthalmic lens may incorporate electronic sensors to detect concentrations of particular chemicals in the ocular fluid of a user. However, the use of embedded electronics in ophthalmic lenses introduces challenges including, for example, a potential requirement for communication with the electronics, for internal and external sensing and/or monitoring, and for control of the electronics and the overall function of the ophthalmic lens, all of which must take place using relatively low power applications due to volume, and area constrains.

Systems which comprise multiple sensors may require an added degree of complexity but may also include added functionality, convenience, and other parameters important to users. Rather than relying on a single input to determine an output, multi-sensor systems may improve reliability, functionality, safety, and convenience, for example, by reducing false positive and false negative determinations for the output. Systems which consider multiple sensor inputs before determining the need for state change are common in other fields. As such, enabling systems that are based on multiple sensors for an ophthalmic lens can result in more energy efficient, safe, reliable, and useful ophthalmic lenses.

Therefore, there is a need for methods to activate and control operations of a processor controlled ophthalmic lens in a safe, personalized, and energy efficient manner.

SUMMARY

Accordingly, the foregoing needs are met, to a great extent, by the system and methods used to personalize and/or calibrate operation and activation protocols controlling a function/component in the energized ophthalmic lens. In accordance with some embodiments of the present disclosure, the system can include an energized ophthalmic lens comprising a system controller and a plurality of sensors in communication with the system controller which can be configured to store operational protocols. Also part of the system, an interactive wireless device in communication with the system controller of the energized ophthalmic lens can be included. The system controller can be configured to receive a signal from the interactive wireless device and modify one or more operational protocols based on the received signal from the interactive wireless device. Moreover, the signal from the interactive wireless device can be a response from a user to a measurement reading from one or more sensors included in the ophthalmic lens. According to some aspects of the disclosure the system may be used to calibrate one or more of the sensors. In some embodiments, the calibration method may further be used to derive operational trouble codes and operational threshold values.

In accordance to other aspects of the disclosure, a method of personalizing operational protocols for the energized ophthalmic lens while the ophthalmic lens is being worn by the user can include: storing one or more operational protocols in a system controller of the energized ophthalmic lens; forming a wireless communication between an interactive wireless device and the energized ophthalmic lens; activating one or more sensors using the system controller of the energized ophthalmic lens; measuring a condition using the one or more sensors of the energized ophthalmic lens; sending a signal relating to the measured condition to the interactive wireless device; responding to the received signal using input from a user entered into the interactive wireless device; and modifying one or more of said operational protocols in the system controller of the energized ophthalmic lens according to the response.

Certain implementations of the method and system have been outlined so that the detailed description below may be better understood. There are, of course, additional implementations that will be described below and which will form the subject matter of the claims.

In this respect, before explaining at least one implementation in detail, it is to be understood that the method and system for the energized ophthalmic lens disclosed is not limited in its application to the details of construction and to the arrangements of the components set forth in the following description or illustrated in the drawings. Also, it is to be understood that the phraseology and terminology employed herein, as well as in the Abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the energized ophthalmic lens. It is understood, therefore, that the claims include such equivalent constructions insofar as they do not depart from the spirit and scope of the present application.

DETAILED DESCRIPTION

Figure 1:
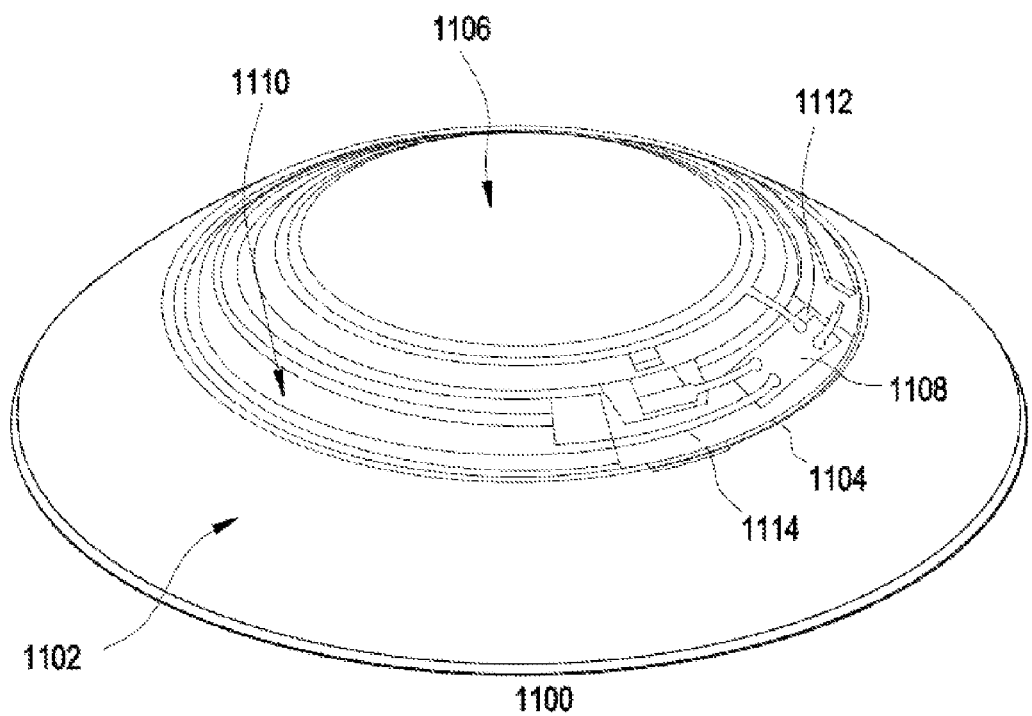
FIG. 1 is a diagrammatic representation an exemplary Energized Ophthalmic Lens in accordance with aspects of the present disclosure.

A system and method for an energized ophthalmic lens used to personalize and/or calibrate operation and activation protocols controlling a function/component of the energized ophthalmic lens are disclosed. The system and methods which may be implemented during the operation and calibration of the energized components in energy efficient manners. In addition, the customizable initiation protocols may be used to gather sensor data generated by two or more sensors with increased relevance and reliability for faster processing.

GLOSSARY

In the description and the claims, various terms may be used for which the following definitions will apply:

Active Lens Insert: as used herein, may refer to an electronic or electromechanical insert device with controls based upon logic circuits.

Energized: as used herein, may refer to the state of being able to supply electrical current to or to have electrical energy stored within.

Energy: as used herein, may refer to the capacity of a physical system to do work. Many uses within this disclosure may relate to the said capacity being able to perform electrical actions in doing work.

Energy Receptor: as used herein, may refer to a medium that can functions as an antenna for receiving wireless energy, such as, for example via radio wave transmission.

Energy Source: as used herein, may refer to device or layer which is capable of supplying Energy or placing a logical or electrical device in an Energized state.

Functionalized Layer Insert: as used herein, may refer to an insert for an ophthalmic device formed from multiple functional layers from which at least a portion of the multiple functional layers are stacked. The multiple layers may have unique functionality for each layer; or alternatively mixed functionality in multiple layers. In some embodiments, the layers can be rings.

Media Insert: as used herein, may refer to a formable or rigid substrate capable of supporting an energization element, such as a battery, within an ophthalmic lens. In some embodiments, the media insert also includes one or more variable optic lenses and communication systems.

Ocular Surface: as used herein, may refer to the anterior surface area of the eye.

Ophthalmic Lens: as used herein, may refer to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the disclosure are soft contact lenses are made from silicone elastomers or hydrogels, which include but are not limited to silicone hydrogels, and fluorohydrogels.

Operation Protocol: as used herein, and sometimes referred to as "customizable Protocols" may refer to one or more operational routine used to control and/or activate electrical components of the energized ophthalmic lens. In some embodiments, operation protocols can include to operational routines for specific modes in which predetermined values or functions can be over overwritten by new inputs including, for example, calibration protocols, safe mode protocol, reset protocol and the like.

Optical Zone: as used herein, may refer to an area of an ophthalmic device or lens through which a wearer of the ophthalmic lens sees after the lens is formed.

Peripheral Zone: as used herein, the term "peripheral zone" or "non-optic zone" may refer to an area of an ophthalmic lens outside of the optic zone of the ophthalmic lens, and therefore outside of a portion of the ophthalmic lens through which a lens wearer sees while wearing the ophthalmic lens on, near or in the eye in a normally prescribed fashion.

Conventional Ophthalmic Lenses are polymeric structures with specific shapes to correct various vision problems as briefly set forth above. To achieve enhanced functionality, various circuits and components may be integrated into these polymeric structures. For example, control circuits, microprocessors, communication devices, power supplies, sensors, actuators, light-emitting diodes, and miniature antennas may be integrated into Ophthalmic Lenses via custom-built optoelectronic components to not only correct vision, but to enhance vision as well as provide additional functionality. Electronic and/or Energized Ophthalmic Lenses may be designed to provide enhanced vision via zoom-in and zoom-out capabilities, or just simply modifying the refractive capabilities of the Ophthalmic Lens. In addition, in some embodiments, electronic and/or Energized Ophthalmic Lenses may be designed to enhance color and resolution, to display textural information, to translate speech into captions in real time, to offer visual cues from a navigation system, for the analysis of biomarkers in ocular fluid (e.g. tear fluid), and/or to provide image processing and internet access.

In some embodiments, the aforementioned functionality may work together to provide a specific function of the Ophthalmic Lens. Properly designed electronics and/or arrangement of electronics on lenses may allow for projecting an image onto the retina, for example, without a variable focus optic lens, provide novelty image displays and even provide alerts. Alternately, or in addition to any of these functions or similar functions, the Ophthalmic Lenses may incorporate sensors to monitor ophthalmic responses and ocular environment conditions.

The Energized Ophthalmic Lens of the present invention can comprise the necessary elements to correct and/or enhance the vision of patients with one or more of the above described vision defects or otherwise perform a useful ophthalmic function. In addition, the Energized Ophthalmic Lens may be utilized simply to enhance normal vision or provide a wide variety of functionality as described above. The Energized Ophthalmic Lens may comprise a variable focus optic lens, an assembled front optic embedded into a contact lens or just simply embedding electronics without a lens for any suitable functionality.

According to aspects of the present disclosure, the Energized Ophthalmic lens comprises system controller, which can actuate a variable-focus optic or any other device or devices configured to implement any number of numerous functions that may be performed. The system controller can be connected to one or more batteries or other power sources, power management circuitry, one or more sensors, clock generation circuitry, control algorithms and circuitry, and lens driver circuitry. The complexity of these components may vary depending on the required or desired functionality of the lens.

According to some aspects of the disclosure, the control of an Energized Ophthalmic Lens may be accomplished using a manually operated external device that can communicate with the Ophthalmic Lens, such as a hand-held remote unit or an Ophthalmic Lens interactive wireless device. For example, a fob, cellular smartphone, tablet, personal computer, and the like, may wirelessly communicate with the powered lens according to input from the wearer. In addition to the hand-held remote device, control protocols of the powered ophthalmic lens may be accomplished via feedback or control signals from the wearer through the ophthalmic environment. For example, sensors built into the lens may detect blinks and/or blink patterns or ophthalmic environment conditions.

In one embodiment, for example, based upon the pattern or sequence of blinks, the powered ophthalmic lens may change state, for example, its refractive power in order to either focus on a near object or a distant object. Interchangeably, blink detection in a powered or electronic ophthalmic lens may be used for other various uses where there is interaction between the user and the Energized Ophthalmic Lens, such as activating another electronic device, or sending a command to another electronic device and vice-versa. For example, blink detection in an Ophthalmic Lens may be used in conjunction with a camera on a computer wherein the camera keeps track of where the eye(s) moves on the computer screen, and when the user executes a blink sequence that it detected, it causes the mouse pointer to perform a command, such as double-clicking on an item, highlighting an item, or selecting a menu item.

Due to volume and contour limitations, execution of the many functionalities and data gathering may be limited by the stored potential of an Energy Source contained in the Ophthalmic Lens and/or the data processing speeds and data storage capacities. As a result and according to aspects of the present disclosure, a system configured to customize Control Protocols to control and calibrate different functionality may be used to overcome the aforementioned limitations. For example, by customizing and calibrating Operational Protocols, the system may capture more focused sensor data. In addition, in some embodiments, the personalized protocols may be implemented to calibrate and diagnose active components of the system in energy efficient manners.

Referring now to FIG. 1, an exemplary contact lens 1100 with a Media Insert comprising a blink detection system in accordance with aspects of the present disclosure is illustrated. The Ophthalmic Lens 1100 may comprise a soft plastic and/or hydrogel portion 1102 which can support, and in some embodiments, encapsulate the Media Insert 1104. The Media Insert 1104 can include a variable lens 1106 which may be activated by the electronics, for example, focusing an image near or far depending on activation.

Integrated circuit 1108 can mount onto a surface of the Media Insert 1104 and connect to Energy Source 1110 (e.g. batteries), lens 1106, and other components as necessary for the system. The integrated circuit 1108 can include a photosensor 1112 and associated photodetector signal path circuits. The photosensor 1112 may face outward through the lens insert and away from the eye, and is thus can be able to receive ambient light. The photosensor 1112 may be implemented on the integrated circuit 1108 (as shown) for example as a single photodiode or array of photodiodes. The photosensor 1112 may also be implemented as a separate device mounted on the Media Insert 1104 and connected with wiring traces 1114.

In some embodiments, an activation signal may result from a user blinking. When the eyelid closes, the Media Insert 1104 including photosensor 1112 is covered, thereby reducing the light level incident on the photosensor 1112. The photosensor 1112 is able to measure the ambient light to determine when the user is blinking. In some embodiments including the blink detection system, an algorithm can be implemented that may allow for more variation in the duration and spacing of the blink sequence to identify activation signals from the user. For example, by timing the start of a second blink based on the measured ending time of a first blink rather than by using a fixed template or by widening the mask "don't care" intervals (0 values).

It will be appreciated that the blink detection algorithm may be implemented in digital logic or in software running on the processor of the system controller 1210. The algorithm logic or system controller 1210 may be implemented in a single application-specific integrated circuit, ASIC, with photodetection signal path circuitry and a system controller, or it may be partitioned across more than one integrated circuit. It is important to note that the blink detection system of the present disclosure has broader uses than for vision diagnostics, vision correction and vision enhancement. These broader uses include utilizing blink detection as a means to control a wide variety of functionality for individuals with physical disabilities.

According to aspects of the disclosure, the blink detection can be included as one of the multiple sensors used to control, activate, and/or gather data. In said embodiments comprising a number of sensors, is preferable to reduce the potential for initiating false actions or false positive triggering using customizable Operation Protocols. In addition, the use of the customizable Operation Protocols can be used to activate sensors in a timely manner and at periods in which measurement data can be useful. Data may become useful, for example, to activate a function, verify a signal, diagnose a condition, and/or calibrate the Energized Ophthalmic Lens.

Further, once data from the one or more sensors is collected according to an Operation Protocol, a decision making process and/or voting scheme can be implemented. This can allow the utilization of the relevant data from multiple sensors to substantially reduce the possibility of changing the state of the Energized Ophthalmic Lens based upon inaccurate, incomplete or erroneous information, changing physiologic conditions, as well as noise and/or interference from internal and external sources. For example, in blink detection, the control system should not change the state of a variable-power optic incorporated into the Energized Ophthalmic Lens based upon a random blinking pattern due to eye irritation or the like. Instead, upon the detection of a blink, a pupil convergence sensor may be activated to verify whether the variable-power optic incorporated should change its state allowing an individual with presbyopia to focus on near distance objects. The pupil convergence sensor's signal can be based on the position of one or both pupils to verify that the blink was intentional.

In a similar embodiment comprising a lid position sensor, eyelid movement may also be utilized as a trigger or verification means for the activation or control of an action. For example, when an individual gazes down to focus on a near distance object, the eyelids tend to droop and thus it may be utilized to change the state of the ophthalmic lens. Once again, if only a single input is utilized, a false action may take place due to the fact that the person is sleepy and their eyelids droop.

The same reasoning can apply to sensors for detecting the presence and locations of objects; namely, emitter-detector pairs, and pupil dilation sensors. All of these sensor readings may be utilized as signals or values for a control protocol to be implemented by various systems incorporated into an electronic or powered Ophthalmic Lens.

In addition to the sensors already mentioned which are intended to detect certain aspects directly related to triggering a state change in an Energized Ophthalmic Lens, other sensors may be used to improve state-change sensors by monitoring ambient conditions, noise, and interference. For example, ambient light may be monitored to improve the accuracy of blink detection, lid position, and pupil diameter sensors. Such sensors may be utilized to augment other sensors, for example, by subtracting common mode noise and interference. Sensor inputs may be used to record history readings which can then considered by a complex decision algorithm, for example, one which considers both accelerometer inputs and eye muscle contraction to determine pupil position. However, by personalizing operational protocols and in some embodiments implementing a voting scheme and/or Boolean logic, more precise and focused measurements can result in addition to eliminating false signals.

As previously mentioned and according to some aspects of the disclosure, it is also important to note that the sensed data, in addition to or in alternate use, may simply be utilized as part of the method of personalizing and calibrating the Ophthalmic Lens using the system described rather than as a triggering event. In other words, it should also be appreciated that a device utilizing such a sensor may not change state in a manner visible to the user; rather the device may simply log data for the modification or one or more operation protocol(s). For example, such a sensor could be used to determine threshold values for a user's iris response to a condition or change monitored.

Figure 2:
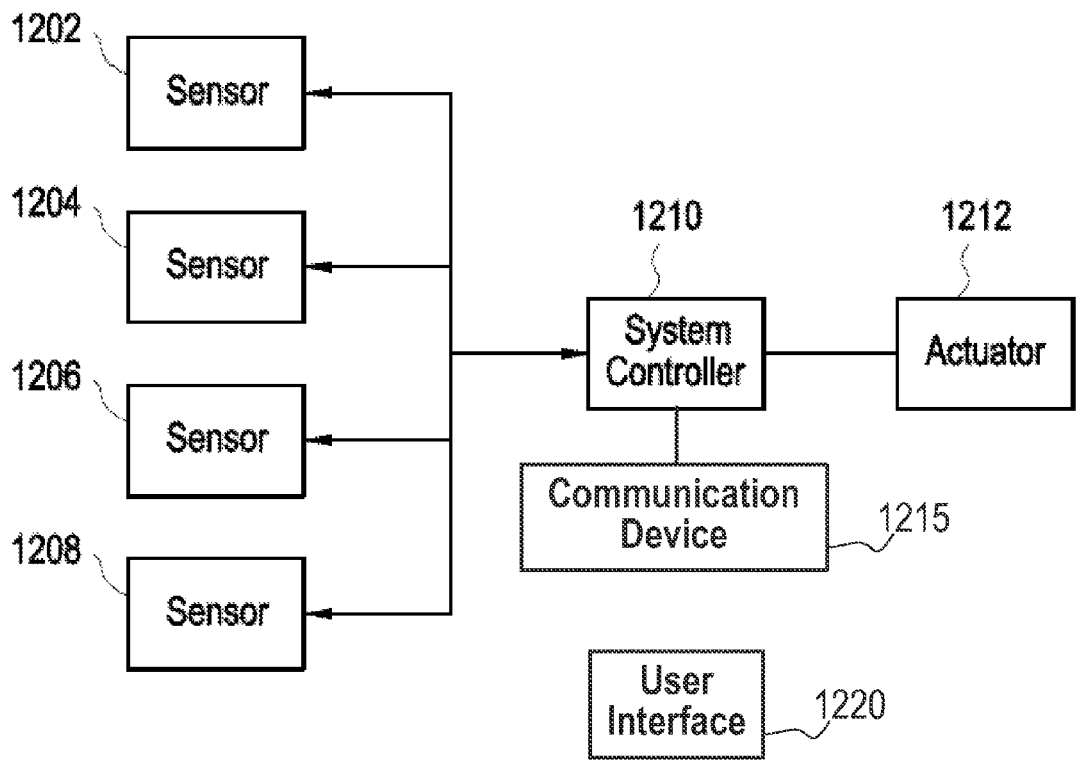
FIG. 2 is a block diagram representation of a system for the control and activation of an energized ophthalmic device having multiple sensors and in wireless communication with an interactive wireless device in accordance with some aspects of the present disclosure.

Referring now to FIG. 2, a block diagram of a system for the control and activation of an energized ophthalmic device having multiple sensors and in wireless communication with an interactive wireless device 1220 is illustrated. According to aspects of the present disclosure, the interactive wireless device 1220 may be used to control/personalize one or more Operation Protocols and/or calibrate electrical components of the Ophthalmic Lens. A Control Protocol can be personalized using a user/eye care practitioner's response through the Ophthalmic Lens interactive wireless device 1220 based on a signal from inputs from one or more of the sensors 1202, 1204, 1206, and 1208. By responding to the measured input signal indicating that a condition or change has been triggered, the response can validate or invalidate the accuracy of the signal. The validation or invalidation data may then be applied to personalize routines and threshold values such as sensor sensitivity. Because ophthalmic conditions of different users will differ, the personalized control protocol may be utilized to personalize/calibrate generic configuration protocols of the system controller to improve decision making performance, data gathering, and power consumption.

As previously mentioned, the sensors 1202, 1204, 1206 and 1208 may comprise any number of potential inputs including blink action, lid position, pupil position, ciliary muscle action, and the like. The number and type of sensors is determined by the application and user. Each sensor 1202, 1204, 1206 and 1208 may have its own signal conditioning contained within the sensor block, a dedicated block, or within the system controller 1210.

The system controller 1210 can accept inputs from each sensor 1202, 1204, 1206 and 1208. It then may perform a voting scheme and compare the input data. Based on these inputs, the system controller 1210 may send the input to the interactive wireless device 1220 through the communication device 1215 to determine/confirm if the state of the actuator 1212 should change. For example, the combination of pupil convergence, lid droop, and an indication from an emitter/detector pair of a close reflection may trigger the system controller 1210 to configure the actuator 1212 to change, for example, a variable-power optic in an ophthalmic lens to be in a near distance focus state. Likewise, the combination of pupil divergence, lid opening, and the indication from the interactive wireless device 1220 may trigger the system controller 1210 to configure the actuator 1212 to change the variable-power optic in an ophthalmic lens to be in a far distance focus state. In addition, alternatively, a signal can be sent by a user through the interactive wireless device 1220 that can overwrite operational Protocol taking place.

Figure 3:
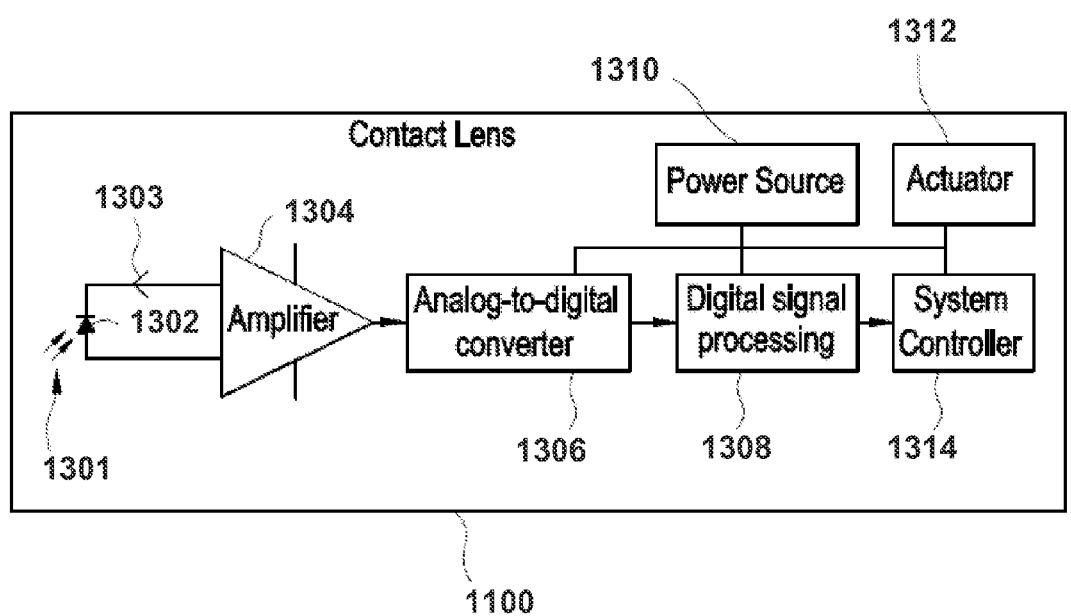
FIG. 3 is a block diagram representation of the exemplary ophthalmic lens of FIG. 1 in accordance with some aspects of the present disclosure.

Referring now to FIG. 3, the exemplary Ophthalmic Lens 1100 of FIG. 1 in accordance with some aspects of the present disclosure is illustrated in block diagram form. According to some embodiments, an interactive wireless device (shown in FIG. 2) can be in wireless connection with the ophthalmic Lens 1100 which may comprise a photosensor 1302, an amplifier 1304, an analog-to-digital converter or ADC 1306, a digital signal processor 1308, a power source 1310, an actuator 1312, and a system controller 1314.

When the Ophthalmic Lens 1100 is placed onto the front surface of a user's eye, the electronic circuitry of the blink detector system may be utilized to implement a blink detection algorithm. Accordingly, the photosensor 1302, as well as the other circuitry, can be configured to detect blinks and/or various blink patterns produced by the user's eye.

In this exemplary embodiment, the photosensor 1302 may be embedded into the Ophthalmic Lens 1100 and receives ambient light 1301, converting incident photons into electrons and thereby causing a current, indicated by arrow 1303, to flow into the amplifier 1304. The photosensor or photodetector 1302 may comprise any suitable device. In one exemplary embodiment, the photosensor 1302 comprises a photodiode.

In a preferred exemplary embodiment, the photodiode is implemented in a complimentary metal-oxide semiconductor (CMOS process technology) to increase integration ability and reduce the overall size of the photosensor 1302 and the other circuitry. The current 103 is proportional to the incident light level and decreases substantially when the photodetector 1302 is covered by an eyelid. The amplifier 1304 creates an output proportional to the input, with gain, and may function as a transimpedance amplifier which converts input current into output voltage. The amplifier 1304 may amplify a signal to a useable level for the remainder of the system, such as giving the signal enough voltage and power to be acquired by the ADC 1306. For example, the amplifier may be necessary to drive subsequent blocks since the output of the photosensor 1302 may be quite small and may be used in low-light environments.

In some embodiments, the amplifier 1304 may be implemented as a variable-gain amplifier, the gain of which may be adjusted by the system controller 1314, in the feedback arrangement described, to maximize the dynamic range of the system. In addition to providing gain, the amplifier 1304 may include other analog signal conditioning circuitry, such as filtering and other circuitry appropriate to the photosensor 1302 and amplifier 1304 outputs. The amplifier 1304 may comprise any suitable device for amplifying and conditioning the signal output by the photosensor 1302. For example, the amplifier 1304 may simply comprise a single operational amplifier or a more complicated circuit comprising one or more operational amplifiers. As set forth above, the photosensor 1302 and the amplifier 1304 can be configured to detect and isolate blink sequences based upon the incident light intensity received through the eye and convert the input current into a digital signal usable ultimately by the system controller 1314. The system controller 1314 is preferably preprogrammed or preconfigured and then calibrated to recognize various personalized blink sequences and/or blink patterns in various light intensity level conditions and provide an appropriate output signal to the actuator 1312. The system controller 1314 can also comprise associated memory.

In this exemplary embodiment, the ADC 1306 may be used to convert a continuous, analog signal output from the amplifier 1304 into a sampled, digital signal appropriate for further signal processing. For example, the ADC 1306 may convert an analog signal output from the amplifier 1304 into a digital signal that may be useable by subsequent or downstream circuits, such as a digital signal processing system or microprocessor 1308. A digital signal processing system or digital signal processor 1308 may be utilized for digital signal processing, including one or more of filtering, processing, detecting, and otherwise manipulating/processing sampled data to permit incident light detection for downstream use. The digital signal processor 1308 may be preprogrammed and calibrated with the blink protocols and/or blink patterns described herein. The digital signal processor 1308 can also comprise associated memory. The digital signal processor 1308 may be implemented utilizing analog circuitry, digital circuitry, software, or a combination thereof.

In the illustrated exemplary embodiment, the digital signal processor 1308 is implemented in digital circuitry. The ADC 1306 along with the associated amplifier 1304 and digital signal processor 108 can be activated at a suitable rate in agreement with the sampling rate previously described, for example every one hundred (100) ms. A power source 1310 may supply power for numerous components comprising the blink detection system. The power may be supplied from a battery, Energy Harvester, or other suitable means as is known to one of ordinary skill in the art. Essentially, any type of power source 1310 may be utilized to provide reliable power for all other components of the system. A calibrated blink sequence may be utilized to change the state of the system and/or the system controller.

In preferred exemplary embodiments, the system controller 1314 may receive input from sources including the interactive wireless device and one or more of a blink detector, eye muscle sensors, biomarker sensors, an accelerometer, temperature sensor and the such. Calibration of the one or more sensors can include programming threshold values specific to the user to allow the positive recognition of an individual's blink patterns and an individual's ciliary muscle signals when performing various actions, for example, focusing on an object far away, or focusing on an object that is near. In some exemplary embodiments, the calibration and personalization of operational protocols to activate an electronic Ophthalmic Lens may give the ability for more focused data management and energy efficient systems. In addition, each preprogrammed method may be crosschecked before activation of the functionality to make sure the change occurs in a safe manner.

The actuator 1312 may comprise any suitable device for implementing a specific action based upon a received command signal. For example, if a blink activation pattern is verified as described above, the system controller 1314 may enable the actuator 1312, such as a variable-optic electronic or powered lens. The actuator 1312 may comprise an electrical device, a mechanical device, a magnetic device, or any combination thereof. The actuator 1312 can receive a signal from the system controller 1314 in addition to power from the power source 1310 and may produce some action based on the signal from the system controller 1314. For example, if the system controller 1314 signal is indicative of the wearer trying to focus on a near object, the actuator 1312 may be utilized to change the refractive power of the electronic ophthalmic lens, for example, via a dynamic multi-liquid optic zone. In an alternate exemplary embodiment, the system controller 1314 may output a signal indicating that a therapeutic agent should be delivered to the eye(s). In this exemplary embodiment, the actuator 1312 may comprise a pump and reservoir, for example, a microelectromechanical system (MEMS) pump. As set forth above, the powered lens of the present invention may provide various functionality; accordingly, one or more actuators may be variously configured to implement the functionality.

Figure 4:
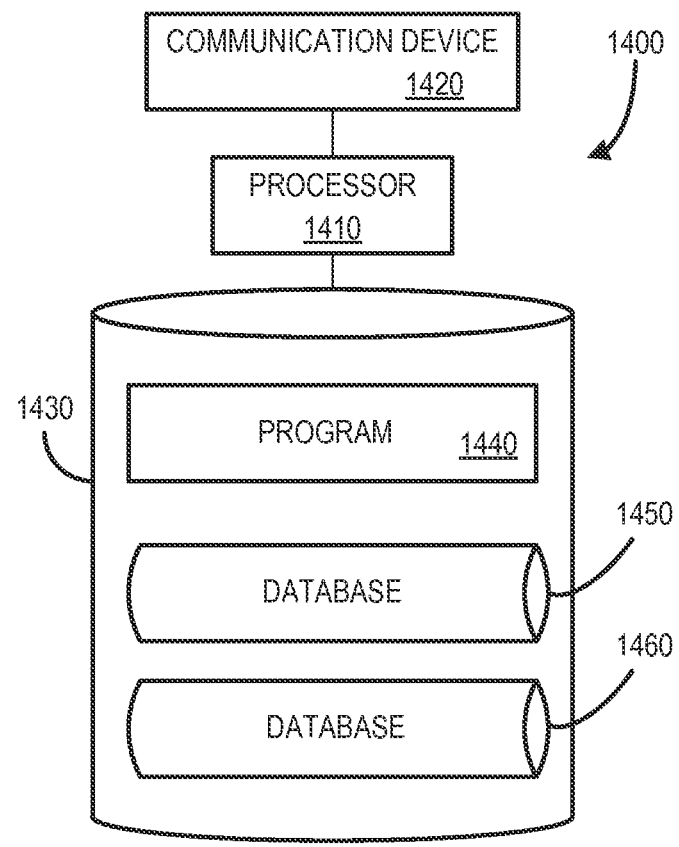
FIG. 4 is a diagrammatic representation of a system controller that may be used to implement some embodiments of the disclosure.

Referring now to FIG. 4, a schematic diagram of an exemplary system controller 1400 that may be used with some embodiments of the present disclosure is illustrated. The system controller 1400 includes a processor 1410, which may include one or more processor components coupled to a communication device 1420. In some embodiments, a system controller 1400 can be used to transmit energy to the energy source placed in the Ophthalmic Lens.

The system controller 1400 can include one or more processors 1410, coupled to a communication device 1420 configured to communicate logical signals via a communication channel. The communication device 1420 may be used to electronically control one or more of: the actuation of a sensor, recording of sensor data, programming and execution of operational protocols, and the transfer of commands to operate a component.

The communication device 1420 may also be used to communicate, for example, with one or more interactive wireless device, metrology device, and/or manufacturing equipment components. The system processor 1410 is also in communication with a storage device 1430. The storage device 1430 may comprise any appropriate information storage device, including combinations of magnetic storage devices (e.g., magnetic tape and hard disk drives), optical storage devices, and/or semiconductor memory devices such as Random Access Memory (RAM) devices and Read Only Memory (ROM) devices.

The storage device 1430 can store a program 1440 for controlling the processor 1410. The processor 1410 performs instructions of the program 1440, and thereby operates in accordance with the present disclosure. For example, the processor 1410 may transmit data including, for example, unique identifier, sensor data, calibration data, operational protocols, user information and other data that can be included for the operation of the ophthalmic lens and/or, in some embodiments, to generate a user profile. Accordingly, the storage device 1430 can also store ophthalmic related data in one or more databases 1450-1460.

Figure 5:
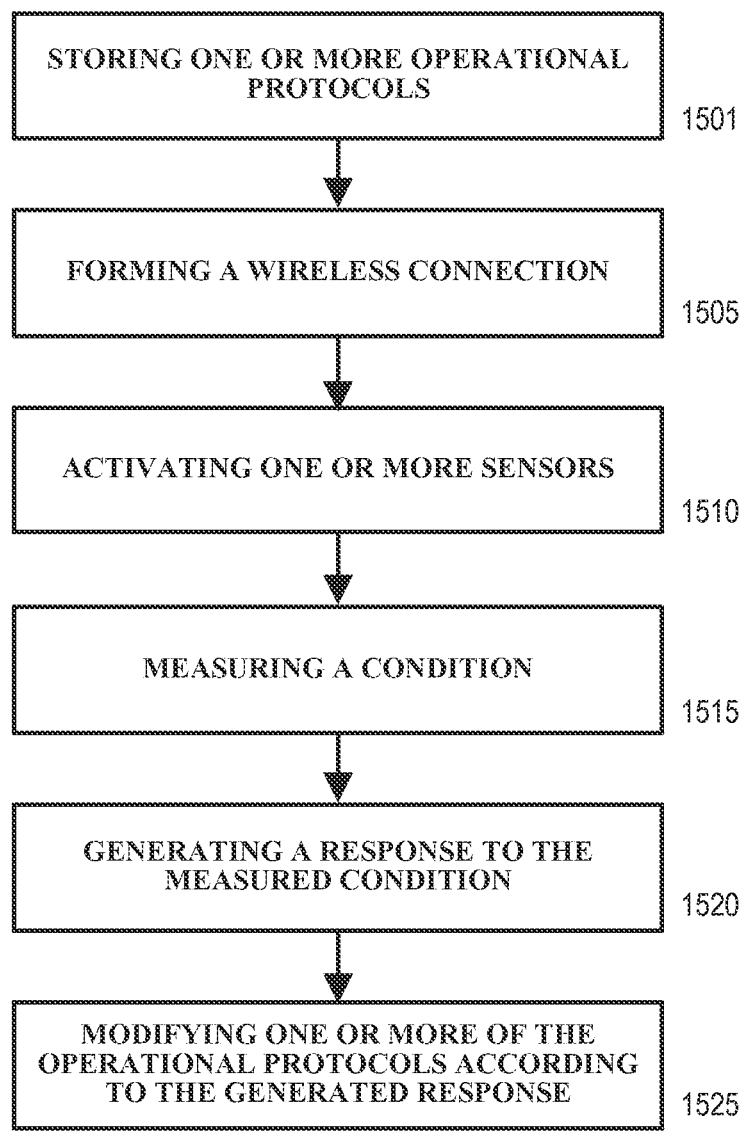
FIG. 5 is a flowchart illustrating exemplary method steps by which a system can personalize one or more pre-programmed operational Protocols according to aspects of the present disclosure.

Referring now to FIG. 5, exemplary method steps which a system controller, for example, system controller 1210 illustrated in FIG. 2, can operate to personalize/calibrate one or more pre-programmed operational Protocols according to aspects of the present disclosures are depicted. Beginning at step 1501, one or more Operational Protocols for energized components of an ophthalmic lens can be preprogrammed in a system controller of the ophthalmic lens. Preprogramming of Operational Protocols can include, for example, power conservation sensor actuating routines, data processing/storage functions, and actuation of active components. At step 1505, a wireless connection can be formed between an Ophthalmic Lens and at least one interactive wireless device. In some embodiments, at step 1510, the interactive wireless device can be useful to activate one or more sensors. However, alternatively, the activation of a sensor within the Ophthalmic Lens may be used to initiate the wireless connection with the interactive wireless device. At step 1515, a condition may be measured using one or more sensors. A condition may include environmental ophthalmic conditions, operational conditions (e.g. troubleshooting), concentrations of biomarkers, temperature, light exposure, and the such. At step 1520, a response to the measured condition can be generated using the interactive wireless device. The response may include verification that a respective action is desired or voiding the action. Moreover, the response may be from one or a combination of interactive wireless devices and include input from a user, an eye care practitioner, and a metrology apparatus.

At step 1525, the response can be used to modify one or more of the originally preprogrammed operational protocols. The modification may include, for example, sensitivity threshold values for one or more of the different sensors, actuation mechanisms, user preferences to the degree of change of an active element, going into a safe mode operation and the such. In preferred systems, the modifications may be performed for calibration to generate a user profile and adjust it periodically as conditions change or recalibration is desired, for example, due to performance changes in the system.

Additional features, advantages, and aspects of the disclosure may be set forth or apparent from consideration of the following detailed description, drawings, and claims. Moreover, it is to be understood that both the foregoing summary of the disclosure and the following detailed description are exemplary and intended to provide further explanation without limiting the scope of the disclosure as claimed.

The invention claimed is:

1. A system for the control and activation of an energized ophthalmic lens, comprising:
an energized ophthalmic lens comprising a system controller and a plurality of sensors in communication with the system controller, the system controller being configured to store operational protocols; and
an interactive wireless device in communication with the system controller of the energized ophthalmic lens,
wherein the system controller is configured to receive a signal from the interactive wireless device and modify one or more operational protocols based on the received signal from the interactive wireless device, and
the signal from the interactive wireless device is a response from a user to a measurement reading from one or more of the plurality of sensors of the ophthalmic lens.

2. The system of claim 1, wherein:
the system controller is further configured to calibrate one or more of the plurality of sensors based on the response from the user to the measurement reading from the one or more of the plurality of sensors of the energized ophthalmic lens.

3. The system of claim 2, wherein:
the system controller is further configured to derive operational trouble codes and operational threshold values from the calibration of said one or more of the plurality of sensors of the energized ophthalmic lens.

4. The system of claim 3, wherein:
the system controller is further configured to execute an operational safe mode protocol upon detection of a measurement reading from one or more of the sensors that is outside the threshold values from the calibration of said one or more of the plurality of sensors of the energized ophthalmic lens.

5. The system of claim 3, wherein:
the system controller is further configured to execute an operational safe mode protocol upon the receipt of a safe mode corresponding signal sent by the interactive wireless device in communication with the energized ophthalmic lens.

6. The system of claim 1, wherein:
the system controller is further configured to select a measurement reading output from measurement readings of said one or more of the plurality of sensors of the energized ophthalmic lens using a preprogrammed voting scheme.

7. The system of claim 1, wherein:
the system controller is further configured to select an operational protocol according to Boolean logic and measurement readings from said one or more of the plurality of sensors of the energized ophthalmic lens.

8. The system of claim 1, wherein:
the system controller is further configured to actuate one or more of the plurality of sensors in response from a signal from an initial input sent by the interactive wireless device in communication with the energized ophthalmic lens.

9. The system of claim 1, wherein:
the interactive wireless device in wireless communication with the energized ophthalmic lens is a frequency operated handheld remote unit.

10. The system of claim 1, wherein:
the interactive wireless device in wireless communication with the energized ophthalmic lens is a smart cellular telephone device.

11. The system of claim 1 wherein:
the interactive wireless device in wireless communication with the energized ophthalmic lens is a personal computer.

12. The system of claim 1, wherein:
the interactive wireless device in wireless communication with the energized ophthalmic lens is a tablet.

13. A method of personalizing operational protocols of an energized ophthalmic lens comprising:
storing one or more operational protocols in a system controller of the energized ophthalmic lens;
forming a wireless communication between an interactive wireless device and the energized ophthalmic lens;
activating one or more sensors using the system controller of the energized ophthalmic lens;
measuring a condition using the one or more sensors of the energized ophthalmic lens;
sending a signal relating to the measured condition to the interactive wireless device;
responding to the received signal using input from a user entered into the interactive wireless device; and
modifying one or more of said operational protocols in the system controller of the energized ophthalmic lens according to the response.

14. The method of claim 13, wherein:
the modification to the one or more operational protocols is performed to calibrate the ophthalmic lens while the ophthalmic lens is being worn by a user.

15. The method of claim 14, wherein:
the calibration includes storing measurement thresholds for the one or more sensors of the ophthalmic lens.

16. The method of claim 15, additionally comprising:
generating a user profile including the stored measurement thresholds for the one or more sensors of the ophthalmic lens.

17. The method of claim 13, wherein:
the signal relating to the measured condition is generated using measurements from the one or more sensors selected using a preprogrammed voting scheme in the system controller of the ophthalmic lens.

18. The method of claim 13, additionally comprising:
selecting a modified operational protocol to change a state of an electrical component the ophthalmic lens.

19. The method of claim 18, wherein:
the selection of the modified operational protocol is done according to according to Boolean logic and readings from the one or more sensors.

20. The method of claim 18, additionally comprising:
activating a safe mode operational protocol through the interactive wireless device in wireless communication with the ophthalmic lens.

* * * * *